United States Patent [19]

Ife et al.

[11] Patent Number: 5,143,920
[45] Date of Patent: Sep. 1, 1992

[54] SUBSTITUTED 4-AMINOQUINOLINE DERIVATIVES AS GASTRIC SECRETION INHIBITORS

[75] Inventors: Robert J. Ife; Thomas H. Brown; Colin A. Leach, all of Stevenage, England

[73] Assignee: SmithKline Beckman Intercredit B.V., Netherlands

[21] Appl. No.: 314,684

[22] Filed: Feb. 23, 1989

[30] Foreign Application Priority Data

Feb. 25, 1988 [GB] United Kingdom ............... 8804443

[51] Int. Cl.$^5$ .................. A61K 31/47; C07D 215/42; C07D 215/44
[52] U.S. Cl. .................. 514/313; 546/159; 546/160; 546/161; 546/162
[58] Field of Search ............... 546/159, 160, 161, 162; 514/313

[56] References Cited

U.S. PATENT DOCUMENTS

| | | | |
|---|---|---|---|
| 2,652,398 | 9/1953 | Kaye | 260/288 |
| 3,391,146 | 7/1968 | Godfrey | 546/159 |
| 3,470,186 | 9/1969 | Hanifin | 546/160 |
| 4,343,804 | 8/1982 | Munson, Jr. et al. | 514/313 |
| 4,806,549 | 2/1989 | Ife et al. | 546/162 |
| 4,806,550 | 2/1989 | Ife et al. | 546/162 |

FOREIGN PATENT DOCUMENTS

| | | | |
|---|---|---|---|
| 0258755 | 3/1988 | European Pat. Off. | 546/159 |
| 0259174 | 3/1988 | European Pat. Off. | |
| 2106612 | 5/1972 | France. | |
| 2047244 | 11/1980 | United Kingdom. | |
| 8801621 | 3/1988 | World Int. Prop. O. | 546/159 |

OTHER PUBLICATIONS

Sen et al., Chem. Abs., vol. 52, No. 16, entry 13732 c-f (1958).
Robins, Chem.. Abs., vol. 94, No. 21, entry 174910c (1981).
McOmie, Protective Groups in Organic Chemistry, (Plenum Press, New York, 1973), pp. 145-147.

Primary Examiner—Robert T. Bond
Assistant Examiner—E. C. Ward
Attorney, Agent, or Firm—Dara L. Dinner; Stuart R. Suter; Edward T. Lentz

[57] ABSTRACT

Substituted 4-aminoquinazoline derivatives of the formula:

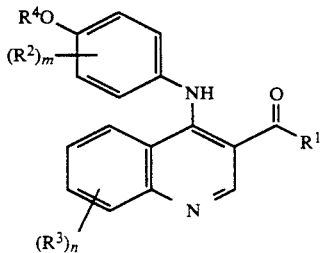

wherein
$R^1$ is hydrogen, $C_{1-6}$ alkyl, $C_{1-6}$ alkoxy, $C_{1-6}$ alkoxy $C_{1-6}$ alkyl,
$C_{3-6}$ cycloalkyl, $C_{3-6}$ cycloalkyl $C_{1-6}$ alkyl, phenyl $C_{1-6}$ alkyl, the phenyl group being optionally substituted;
$R^2$ is hydrogen, $C_{1-6}$ alkyl, $C_{1-6}$ alkoxy, amino, $C_{1-6}$ alkylthio, halogen, cyano, hydroxy, $C_{1-6}$ alkanoyl or trifuromethyl;
m is 1 to 3;
$R^3$ is hydrogen, $C_{1-6}$ alkyl, phenyl, $C_{1-6}$ alkoxy, $C_{1-6}$ alkylthio, $C_{1-6}$ alkanoyl, amino, $C_{1-6}$ alkylamino, ci-$C_{1-6}$ alkylamino, halogen, trifluoromethyl or cyano;
n is 1 or 2; and
$R^4$ is hydrogen; or a salt thereof are useful as inhibitors of gastric acid secretion.

18 Claims, No Drawings

SUBSTITUTED 4-AMINOQUINOLINE DERIVATIVES AS GASTRIC SECRETION INHIBITORS

The present invention relates to novel substituted quinoline derivatives, processes for their preparation, intermediates useful in their preparation, pharmaceutical compositions containing them and their use in therapy.

Substituted quinoline derivatives having activity as inhibitors of gastric acid secretion are known in the art. In particular, U.S. Pat. No. 4343804 and EP 259174-A disclose series of 4-phenylaminoquinoline compounds in which the phenyl ring is optionally substituted by a range of substituents.

It has now been found that a novel class of compounds falling within the above 2 broad disclosures, namely 4-phenylaminoquinolines in which the phenyl ring is substituted by a 4-hydroxy group are particularly potent inhibitors of gastric acid secretion.

Accordingly, the present invention provides, in a first aspect, a compound of structure (I):

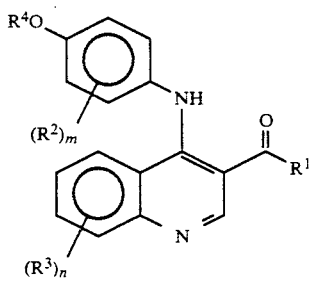

(I)

in which
R$^1$ is hydrogen, C$_{1-6}$alkyl, C$_{1-6}$alkoxy, C$_{1-6}$alkoxyC$_{1-6}$-alkyl, C$_{3-6}$cycloalkyl, C$_{3-6}$cycloalkylC$_{1-6}$alkyl, phenylC$_{1-6}$alkyl, the phenyl group being optionally substituted;
R$^2$ is hydrogen, C$_{1-6}$alkyl, C$_{1-6}$alkoxy, amino, C$_{1-6}$alkylthio, halogen, cyano, hydroxy, C$_{1-6}$alkanoyl or trifluoromethyl;
m is 1 to 3;
R$^3$ is hydrogen, C$_{1-6}$alkyl, phenyl, C$_{1-6}$alkoxy, C$_{1-6}$alkylthio, C$_{1-6}$alkanoyl, amino, C$_{1-6}$alkylamino, di-C$_{1-6}$alkylamino, halogen, trifluoromethyl or cyano;
n is 1 or 2; and
R$^4$O- is hydroxy or a bioprecursor of a hydroxy group, or a salt thereof.

Suitably, R$^1$ is hydrogen, C$_{1-6}$alkyl, C$_{1-6}$alkoxy, C$_{1-6}$alkoxyC$_{1-6}$alkyl, C$_{3-6}$cycloalkyl, C$_{3-6}$cycloalkylC$_{1-6}$alkyl, phenylC$_{1-6}$alkyl, the phenyl group being optionally substituted. Preferably R$^1$ is hydrogen, C$_{1-6}$alkyl or C$_{1-6}$alkoxy. Most preferably R$^1$ is C$_{1-6}$alkyl, in particular ethyl, n-propyl or i-propyl.

Suitably m is 1 to 3, preferably m is 1 or 2; most preferably m is 1.

Suitably R$^2$ is hydrogen, C$_{1-6}$alkyl, C$_{1-6}$alkoxy, amino, C$_{1-6}$alkylthio, halogen, cyano, hydroxy, C$_{1-6}$alkanoyl or trifluoromethyl.

Preferably R$^2$ is hydrogen, C$_{1-6}$alkyl or C$_{1-6}$alkoxy; most preferably R$^2$ is C$_{1-6}$alkyl or C$_{1-6}$alkoxy in particular methyl or methoxy.

Preferably at least one group R$^2$ is in the 2-position of the phenyl ring (i.e. ortho to the bond joining the ring to the nitrogen atom).

Suitably, n is 1 or 2, preferably n is 1; preferably R$^3$ is in the 8-position of the quinoline ring.

Suitably R$^3$ is hydrogen, C$_{1-6}$alkyl, phenyl, C$_{1-6}$alkoxy, C$_{1-6}$alkylthio, C$_{1-4}$alkanoyl, amino, C$_{1-6}$alkylamino, diC$_{1-6}$alkylamino, halogen, trifluoromethyl or cyano.

Preferably R$^3$ is hydrogen, C$_{1-6}$alkyl or C$_{1-6}$alkoxy, for example, methyl or methoxy.

Suitably R$^4$O- is a bioprecursor of a hydroxy group that is to say a group which is converted to a hydroxy group on administration to a subject. Preferably R$^4$O-is, for example, C$_{1-6}$alkoxy, aryl C$_{1-6}$alkoxy (for example OCH$_2$Ph), C$_{1-6}$alkanoyloxy (for example OCOCH$_3$ or OCOC(CH$_3$)$_3$), arylC$_{1-6}$alkanoyloxy (for example OCOCH$_2$Ph), arylsulphonyloxy (for example toluenesulphonyloxy) or alkylsulphonyloxy (for example methanesulphonyloxy); most preferably R$^4$O- is hydroxy.

C$_{1-6}$alkyl groups (either alone or as part of another group) ca be straight or branched.

Phenyl C$_{1-6}$alkyl groups include for example the benzyl, phenylethyl, phenylpropyl and phenylbutyl groups, and such groups in which the alkyl position thereof is branched e.g. 1-methylbenzyl.

Substituted phenyl C$_{1-6}$alkyl groups R$^1$ include, for example, phenyl groups substituted by 1 to 3 substituents R$^2$ as hereinbefore described.

It will be appreciated that compounds of structure (I) in which one or more of R$^1$ to R$^3$ is a C$_{3-6}$alkyl group (either alone or as part of another group for example a benzyl or phenethyl group) may contain an asymmetric centre due to the presence of the C$_{3-6}$alkyl group. Such compounds will exist as two (or more) optical isomers (enantiomers). Both the pure enantiomers, racemic mixtures (50% of each enantiomer) and unequal mixtures of the two are included within the scope of the present invention. Further, all diastereomeric forms possible (pure enantiomers and mixtures thereof) are within the scope of the invention.

Compounds of structure (I) can form pharmaceutically acceptable acid addition salts with suitable organic and inorganic acids the nature of which will be apparent to persons skilled in the art. For example, pharmaceutically acceptable salts can be formed by reaction with hydrochloric, sulphuric, or phosphoric acids; aliphatic, aromatic or heterocyclic sulphonic acids or carboxylic acids such as for example, citric, maleic or fumaric acids.

In a further aspect, the present invention provides a process for the preparation of a compound of structure (I) which comprises (a) reaction of a compound of structure (II) with a compound of structure (III):

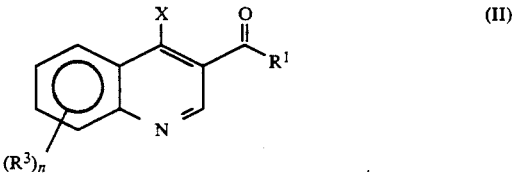

(II)

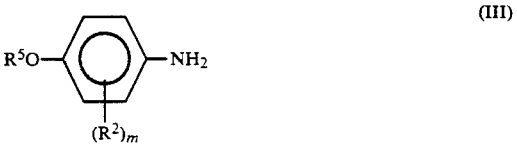

(III)

in which $R^1$, $R^2$, $R^3$, n and m are as described for structure (I), $R^5$ is hydrogen or a protecting group and X is a group displaceable by an amine;

(b) reduction of a compound of structure (IV):

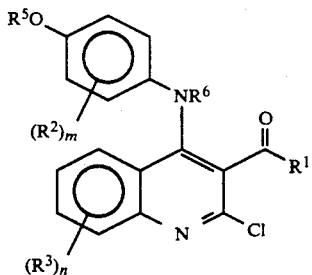
(IV)

in which $R^1$, $R^2$, $R^3$ n and m are as described for structure (I), $R^5$ is a hydrogen or a protecting group and $R^6$ is hydrogen or a nitrogen protecting group;

(c) for compounds of structure (I) in which $R^1$ is other than $C_{1-6}$alkoxy, oxidation of a compound of structure (V):

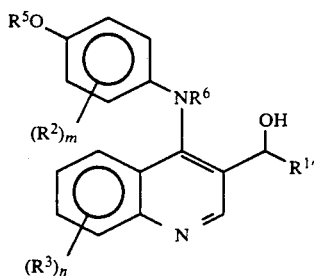
(V)

in which $R^2$, $R^3$, n and m are as described for structure (I), $R^{1'}$ is a group $R^1$ other than $C_{1-6}$alkoxy and $R^5$ and $R^6$ are as described for structure (IV); and thereafter if desired,

- ○ removing any protecting groups;
- ○ converting a group $R^1$ into another group $R^1$;
- ○ forming a salt.

Suitable groups X displaceable by an amine, include for example, halo moieties, aryl or alkylsulphonates, for example, toluene-p-sulphonate or methane sulphonate, alkylthio, alkylsulphonyl, alkylsulphinyl, alkoxy or aryloxy groups. Preferably X is halo, for example, chloro or bromo, or an aryloxy moiety such as phenoxy.

Suitable hydroxy protecting groups $R^5$ and nitrogen protecting groups $R^6$ will be apparent to those skilled in the art for example as described in "Protective Groups in Organic Synthesis" T.W. Greene, 1981 (Wiley).

The reaction between compounds of structure (II) and compounds of structure (III) is carried out in an organic solvent at a temperature of between ambient and reflux temperature of the solvent used. Suitable solvents include, for example, tetrahydrofuran, dioxan or anisole. Preferably the reaction is carried out at reflux temperature in dioxan as a solvent.

The reduction of a compound of structure (IV) is carried out by for example hydrogenation, over a noble metal catalyst in a suitable solvent. Suitably the reaction is carried out over a palladium on carbon catalyst in ethanol as a solvent.

The compounds of structure (IV) can be prepared from the corresponding compounds of structure (VI):

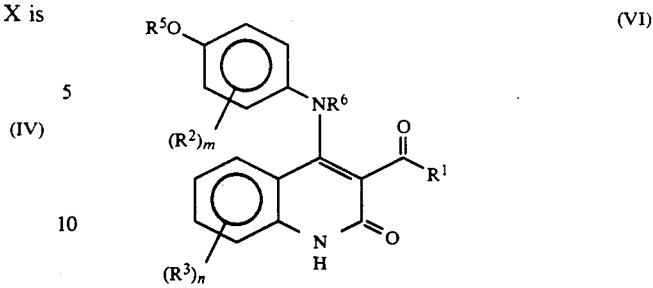
(VI)

in which $R^1$, $R^2$, $R^3$, $R^5$, $R^6$, n and m are as hereinbefore described, by reaction with, for example, phosphorus oxychloride.

The oxidation of a compound of structure (V) is carried out in a suitable solvent in the presence of an oxidising agent. Suitable oxidising agents include, for example, manganese dioxide or chromium trioxide.

Suitable interconversions of groups $R^1$ will be apparent to those skilled in the art, for example compounds of structure (I) in which $R^1$ is $C_{2-6}$alkyl, $C_{3-6}$cycloalkyl$C_{2-6}$alkyl or optionally substituted phenyl$C_{2-6}$alkyl can be prepared by alkylation of the following compounds of structure (IA):

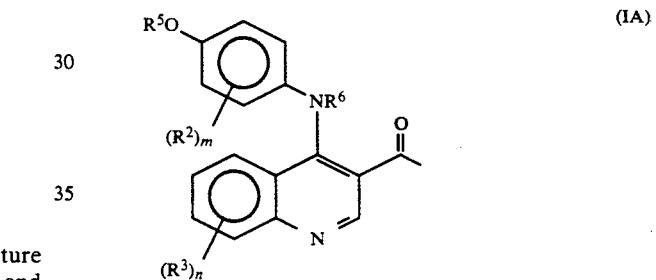
(IA)

in which $R^2$, $R^3$, n and m are as described for structure (I) and $R^5$ and $R^6$ are as described for structure (IV).

The alkylation of compounds of structure (IA) is carried out in the presence of an alkylating agent in a suitable organic solvent at a temperature of between ambient and reflux temperature of the solvent used in the presence of a strong base. Suitable alkylating agents include, for example alkyl or aralkyl halides such as methyl or benzyl iodide and dialkyl sulphates such as dimethyl or diethylsulphate. Suitable strong bases include, for example, sodium hydride, lithium diisopropylamide or dimsyl sodium (the sodium salt of dimethyl sulphoxide). Subsequent removal of any protecting groups present affords the desired compounds of structure (I).

The intermediates of structure (II), (IV), (V) and (VI) can be prepared by standard techniques.

The intermediates of structure (III) are commercially available or can be prepared by standard techniques.

The compounds of structure (I) and their pharmaceutically acceptable salts exert an anti-secretory effect by inhibition of the gastrointestinal $H^+K^+$ATPase enzyme (Fellenius, E., Berglindh, T., Sachs, G., Olke, L., Elander, B., Sjostrand, S.E., and Wallmark, B., 1981, Nature, 290, 159–61).

In a further aspect therefore the present invention provides compounds of structure (I) and pharmaceutically acceptable salts thereof for use in therapy. The compounds of structure (I) and their pharmaceutically acceptable salts inhibit exogenously and endogenously stimulated gastric acid secretion and are useful in the treatment of gastrointestinal diseases in mammals, in particular humans. Such diseases include, for example, gastric and duodenal ulcers, aspiration pneumonitis and Zollinger-Ellison Syndrome.

Further, the compounds of structure (I) can be used in the treatment of other disorders where an anti-secretory effect is desirable for example in patients with gastritis, NSAID induced gastritis, acute upper intestinal bleeding, in patients with a history of chronic and excessive alcohol consumption, and in patients with gastro oesophageal reflux disease (GERD).

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The present invention also provides a method of inhibiting gastric acid secretion which comprises administering to a mammal in need thereof an effective amount of a compound of the formula (I) or a pharmaceutically acceptable salt thereof; and a method of treatment of diseases of the stomach or intestine based on increased acid secretion which comprises administering to a mammal in need thereof an effective amount of a compound of the formula (I) or a pharmaceutically acceptable salt thereof.

The pharmaceutically acceptable compounds of the invention will normally be administered to a subject for the treatment of gastro-intestinal diseases and other conditions caused or exacerbated by gastric acidity. The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day. Suitably the compounds will be administered for a period of continuous therapy, for example for a week or more.

In addition, the compounds of the present invention can be co-administered with further active ingredients, such as antacids (for example magnesium carbonate or hydroxide and aluminium hydroxide), non-steroidal antiflammatory drugs (for example indomethacin, aspirin or naproxen), steroids, or nitrite scavengers (for example ascorbic acid or aminosulphonic acid), or other drugs used for treating gastric ulcers (for example pirenzipine, prostanoids for example 16,16 dimethyl PGE$_2$, or histamine H$_2$-antagonists (for example, cimetidine).

The following examples illustrate the invention. Temperatures are recorded in degrees centigrade.

EXAMPLE 1

Preparation of 3-butyryl-4-(4-hydroxyphenylamino)-8-methoxyquinoline

3-Butyryl-4-chloro-8-methoxyquinoline (2 g, 8 mmol), 4-aminophenol (1.24 g, 11 mmol) and 1,4-dioxan (50 ml) were heated at reflux for 2 hours, then the solid filtered off and converted to free base. Recrystallisation from ethanol and then methanol gave 3-butyryl-4-(4-hydroxyphenylamino)-8-methoxyquinoline (1.6 g), m.p. 270°–272°.

$C_{20}H_{20}N_2O_3$

Found; C 71.22, H 5.87, N 8.26.
Requires; C 71.41, H 5.99, N 8.33.

EXAMPLE 2

Preparation of 3-butyryl-4-(4-hydroxy-2-methylphenylamino)-8-methoxyquinoline

3-Butyryl-4-chloro-8-methoxyquinoline (3.95 g, 15 mmol), 4-amino-3-methylphenol (2.46 g, 20 mmol) and 1,4-dioxan (15 ml) were warmed briefly to reflux, then the solid filtered off and washed with ethyl acetate. Conversion to free base and recrystallisation from ethanol gave 3-butyryl-4-(4-hydroxy-2-methylphenylamino)-8-methoxyquinoline (1.79 g, 34%), m.p. 252°–253°.

$C_{21}H_{22}N_2O_3.0.15H_2O$

Found; C 71.41, H 6.42, N 7.90.
Requires; C 71.43, H 6.37, N 7.93.

EXAMPLE 3

Preparation of
3-butyryl-4-(4-hydroxy-2,6-dimethylphenylamino)-8-methoxyquinoline 4-Amino-3,5-dimethylphenol (1.8 g, 1.3 mmol) and 3-butyryl-4-chloro-8-methoxyquinoline (2.6 g, 10 mmol) were heated together under reflux in 1,4-dioxan (50 ml) for 2 hours. The solvent was evaporated and the residue dissolved in dichloromethane, washed with water, sodium hydrogen carbonate solution and brine, dried and evaporated to a yellow solid which on recrystallisation from ethanol, followed by methanol, afforded 3-butyryl-4-(4-hydroxy-2,6-dimethylphenylamino)-8-methoxyquinoline as yellow crystals, m.p. 247°–8°.

$C_{22}H_{24}N_2O_3$

Found; C 72.28, H 6.62, N 7.66.
Requires; C 72.50, H 6.64, N 7.69.

EXAMPLE 4

Preparation of
3-butyryl-4-(4-hydroxy-3-fluorophenylamino)-8-methoxyquinoline

2-Fluoro-4-aminophenol (0.8 g, 6 mmol) and 3-butyryl-4-chloro-8-methoxyquinoline (1.5 g, 5.7 mmol) were heated together under reflux in 1,4-dioxan (50 ml) for 1 hour. The solvent was evaporated and the residue was dissolved in dichloromethane, washed with water, sodium hydrogen oarbonate solution and brine then dried and evaporated. The residue was recrystallised from methanol-water to afford 3-butyryl-4-(3-fluoro-4-hydroxyphenylamino)-8-methoxyquinoline, m.p. 266°–268°.

$C_{20}H_{19}FN_2O_3 \cdot 0.02CH_2Cl_2$

Found; C 67.34, H 5.25, N 7.71.
Requires; C 67.53, H 5.39, N 7.87.

EXAMPLE 5

Preparation of
3-butyryl-4-(3-chloro-4-hydroxyphenylamino)-8-methoxyquinoline hydrochloride 3-Butyryl-4-chloro-8-methoxyquinoline (2.64 g, 10 mmol), 2-chloro-4-aminophenol (1.58 g, 11 mmol) and 1,4-dioxan (20 ml) were warmed briefly to reflux, cooled, and the solid filtered off. Recrystallisation from pyridine gave 3-butyryl-4-(3-chloro-4-hydroxyphenylamino)-8methoxyquinoline hydrochloride (1.40 g, 34%), m.p. 267°–269° (dec).

$C_{20}H_{19}ClN_2O_3 \cdot HCl$

Found; C 58.99, H 5.03, N 6.83, Cl−8.40.
Requires; C 58.98, H 4.95, N 6.88, Cl−8.70.

EXAMPLE 6

Preparation of
3-butyryl-4-(4-hydroxy-2-methylphenylamino)-8-fluoroquinoline

A. Preparation of ethyl 2-butyryl-3-(2-fluorophenyamino)-acrylate

2-Fluoroaniline (25 g, 0.23 mol) and ethyl 2-butyryl-3-ethoxyacrylate (48 g, 0.23 mol) were heated at 150° for 2 hours, then diluted with petroleum ether and left to stand overnight. Filtration and washing gave ethyl 2-butyryl-3-(2-fluorophenylamino)acrylate (37.5 g), m.p. 60°–62°.

B. Preparation of 3-butyryl-8-fluoro-4(1H)-quinolone

Ethyl 2-butyryl-3-(2-fluorophenylamino)acrylate (37 g, 0.13 mol) was added in portions to boiling diphenyl ether (450 ml), then heated at reflux for 1.5 hours. After partial cooling the mixture was diluted with petroleum ether (50 ml). Filtration and washing with petroleum ether gave 3-butyryl-8-fluoro-4(1H)-quinolone (26.5 g), m.p. 176°–178°.

C. Preparation of 3-butyryl-4-chloro-8-fluoroquinoline

3-Butyryl-8-fluoro-4(1H)-quinolone (2.7 g, 12 mmol) and phosphoryl chloride (40 ml) were heated at reflux for 3 hours. Excess phosphoryl chloride was evaporated in vacuo. the residue poured onto ice and neutralised with aqueous ammonia. Filtration and washing with water gave 3-butyryl-4-chloro-8-fluoroquinoline ((1.75 g), m.p. 57°–60°.

D. Preparation of
3-butyryl-4-(4-hydroxy-2-methylphenylamino)-8-fluoroquinoline 3-butyryl-4-chloro-8-fluoroquinoline (1.75 g, 7 mmol), 4-amino-3-methylphenol (1.3 g, 10 mmol) and 1,4-dioxan (50 ml) were heated at reflux for 6.5 hours, then the solvent evaporated and the product converted to free base. Recrystallisation from methanol gave 3-butyryl-4-(4-hydroxy-2-methylphenylamino)-8-fluoroquinoline (1.2 g), m.p. 205°–207°.

$C_{20}H_{19}FN_2O_2$

Found; C 70.75, H 5.70, N 8.21.
Requires; C 70.99, H 5.66, N 8.28.

EXAMPLE 7

Preparation of
3-butyryl-4-(4-hydroxy-2-methylphenylamino)-8-acetylquinoline

A. Preparation of ethyl 2-butyryl-3-(2-acetylphenylamino)-acrylate

A mixture of ethyl 2-butyryl-3-ethoxyacrylate (23.5 g, 0.11 mol) and 2'-aminoacetophenone (13.5 g, 0.1 mol) was warmed on a steam bath for 10 minutes. Crystallisation from petroleum ether gave ethyl 2-butyryl-3-(2-acetylphenylamino)acrylate as a mixture of E/Z isomers (14.9 g, 49%).

B. Preparation of 3-butyryl-8-acetyl-4(1H)-quinolone

Ethyl 2-butyryl-3-(2-acetylphenylamino)acrylate (14.8 g, 48.8 mmol) was added to boiling diphenyl ether (50 ml) and heated at reflux for 3.5 hours. After cooling, the solution was poured into ether, and the solid filtered off and washed with ether to obtain 3-butyryl-8-acetyl-4(1H)-quinolone (8.8 g), contaminated with some diphenyl ether. This material was used without further purification.

C. Preparation of 3-butyryl-4-chloro-8-acetylquinoline

A solution of 3-butyryl-8-acetyl-4(1H)-quinolone (8.4 g) in phosphoryl chloride (30 ml) was heated at reflux for 1 hour, then poured onto ice and the product extracted into ether. Drying and evaporation gave crude 3-butyryl-4-chloro-8-acetylquinoline as a dark solid, which was used without further purification.

D. Preparation of 3-butyryl-4-(4-hydroxy-2-methylphenylamino)-8-acetylquinoline

A solution of 3-butyryl-4-chloro-8-acetylquinoline (2.0 g) and 4-amino-3-methylphenol (1.23 g, 10 mmol) in 1,4-dioxan (25 ml) was warmed briefly to reflux, then the dioxan evaporated. Chromatography (silica, 4–6% methanol in dichloromethane) and recrystallisation from ethyl acetate gave 3-butyryl-4-(4-hydroxy-2-methylphenylamino)-8-acetylquinoline (0.65 g), m.p. 183°–185°.

$C_{22}H_{22}N_2O_3.0.2H_2O$

Found; C 72.19, H 6.01, N 7.59.
Requires; C 72.19, H 6.17, N 7.65.

EXAMPLE 8

Preparation of 3-butyryl-4-(4-acetoxy-2-methylphenylamino)-8-methoxyquinoline

3-Butyryl-4-(4-hydroxy-2-methylphenylamino)-8-methoxyquinoline (1.75 g, 5 mmol) was dissolved in a mixture of acetic anhydride (10 ml) and pyridine (10 ml), stirred for 18 hours at room temperature, then the solvent evaporated, the product dissolved in dichloromethane and washed with aqueous sodium bicarbonate. Drying, evaporation, and recrystallisation from ethyl acetate/petroleum ether gave 3-butyryl-4-(4-acetoxy-2-methylphenylamino)-8-methoxyquinoline (1.55 g, 79%), m.p. 167°–169°.

$C_{23}H_{24}N_2O_4$

Found; C 70.23, H 6.00, N 7.10.
Requires; C 70.39, H 6.16, N 7.14.

EXAMPLE 9

Ethyl 8-methoxy-4-(4-hydroxy-2-methylphenylamino)-quinoline-3-carboxylate

Ethyl 8-methoxy-4-chloroquinoline-3-carboxylate (2.6 g, 0.0098 mol) and 4-hydroxy-2-methylaniline (2.4 g, 0.0196 mol) in ethanol (150 ml) were heated under reflux for 30 minutes. The solvent was evaporated under reduced pressure. The residue was dissolved in chloroform and extracted with 2N hydrochloric acid (3×100 ml). On basification of the chloroform extracts, a solid precipitated out, this was collected by filtration and dried. Recrystallisation from dimethylformamide gave the title compound. Yield=2.52 g, m.p. 277°–279° C.

$C_{20}H_{20}N_2O_4$

Found; C 68.12, H 5.84, N 8.09.
Requires; C 68.17, H 5.72, N 7.95.

EXAMPLE 10

Preparation of 3-butyryl-4-(4-propanoyloxy-2-methylphenylamino)-8-methoxyquinoline 3-Butyryl-4-(4-hydroxy-2-methylphenylamino)-8-methoxyquinoline (2.0 g, 5.7 mmol) was suspended in pyridine (25 ml), propionic anhydride (25 ml) added, and the mixture stirred for 17 hours at room temperature; the solid slowly dissolved to give a clear solution. Evaporation of the pyridine and recrystallisation from ethyl acetate/petroleum ether gave 3-butyryl-4-(4-propanoyloxy-2-methylphenylamino)-8-methoxyquinoline (2.08 g, 90%), m.p. 163°–165°.

$C_{24}H_{26}N_2O_4.0.25H_2O$

Found; C 70.11, H 6.43, N 6.74.
Requires; C 70.14, H 6.50, N 6.82.

EXAMPLE 11

Preparation of 3-butyryl-4-(4-isobutyryloxy-2-methylphenylamino)-8-methoxyquinoline 3-Butyryl-4-(4-hydroxy-2-methylphenylamino)-8-methoxyquinoline (2.0 g, 5.7 mmol) was suspended in pyridine (25 ml), isobutyryl choride (5 ml) added, and the mixture stirred for 17 hours at room temperature; the solid rapidly dissolved to give a clear solution. The pyridine was evaporated, and the residue taken up in dichloromethane and washed with aqueous sodium bicarbonate and brine, dried and evaporated. Recrystallisation from isopropyl ether gave 3-butyryl-4-(4-isobutyryloxy-2-methylphenylamino)-8-methoxyquinoline (0.87 g, 36%), m.p. 123°–125°.

$C_{25}H_{28}N_2O_4.0.5H_2O$

Found; C 69.83, H 6.59, N 6.41.
Requires; C 69.91, H 6.80, N 6.52.

EXAMPLE 12

Preparation of 3-isobutyryl-4-(4-hydroxy-2-methylphenylamino)-8-methoxyquinoline A solution of 3-isobutyryl-4-chloro-8-methoxyquinoline (1.32 g, 5 mmol) and 4-amino-3-methylphenol (0.62 g, 5 mmol) in dioxan (50 ml) was heated at reflux for 1 hour, then cooled and the solid filtered off. This was taken up in a hot mixture of ethanol and tributylamine, cooled, and the solid filtered off. Recrystallisation from ethanol gave 3-isobutyryl-4-(4-hydroxy-2-methylphenylamino)-8-methoxyquinoline (0.97 g, 55%), m.p. 243°–5°.

$C_{21}H_{22}N_2O_3.0.15H_2O$

Found; C 71.49, H 6.06, N 7.95.
Requires; C 71.43, H 6.36, N 7.93.

EXAMPLE 13

Preparation of
3-butyryl-4-(4-hydroxy-3,5-dimethylphenylamino)-8-methoxyquinoline

A. Preparation of 2,6-dimethyl-4-aminophenol

Sulphanilic acid (43.3 g, 0.25 mol) and sodium carbonate (13.25 g, 0.125 mol) were dissolved in water (250 ml) and cooled to 15° C. Sodium nitrite (18.63 g, 0.27 mol) in water (100 ml) was added in one portion, and the mixture added immediately to concentrated hydrochloric acid (53 ml) and ice (300 g), with stirring. After 30 minutes, the resulting suspension was added to an ice-cold solution of 2,6-dimethylphenol (30.54 g, 0.25 mol) and sodium hydroxide (55 g) in water (550 ml), stirring vigorously. After 2 hours, the temperature was raised to 50°, and sodium dithionite (115 g, 0.66 mol) added portionwise. On heating to 75° the red colour discharged, and after a further 10 minutes, the solution was cooled to room temperature. The resulting white solid was filtered, washed and dried to give the title compound (27.33 g), m.p. 135°–7°.

B. Preparation of
3-butyryl-4-(3,5-dimethyl-4-hydroxyphenylamino)-8-methoxyquinoline 2,6-Dimethyl-4-aminophenol (0.78 g, 5.69 mmol) and 3-butyryl-4-chloro-8-methoxyquinoline (1.0 g, 3.79 mmol) in dioxan (35 ml) were refluxed under nitrogen for 2.5 hours. The solvent was evaporated, and the residue treated with saturated sodium bicarbonate solution and chloroform. The resulting solid was filtered, washed with chloroform and water, boiled in methanol and filtered again to give the title compound (0.84 g) m.p. 287°–9° (dec).

$C_{22}H_{24}N_2O_3 \cdot 0.075 CHCl_3$ 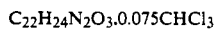

Found; C 71.01, H 6.49, N 7.43.
Requires; C 71.00, H 6.50, N 7.50.

EXAMPLE 14

Preparation of
3-butyryl-4-(4-hydroxy-3,5-difluorophenylamino)-8-methoxyquinoline

A. Preparation of 2,6-difluoro-4-aminophenol 2,6-Difluoro-4-nitrophenol (1.75 g, 10 mmol) and 10% palladium on carbon catalyst (0.3 g) in ethanol (100 ml) were shaken in a closed vessel under an initial hydrogen pressure of 3.5 bar. When hydrogen uptake was complete, the catalyst was filtered off, and the filtrate evaporated to a solid, triturated with petroleum ether, filtered, washed and dried to give the title compound (1.31 g), m.p. indeterminate.

B. Preparation of
3-butyryl-4-(3,5-difluoro-4-hydroxyphenylamino)-8-methoxyquinoline 2,6-Difluoro-4-aminophenol (1.49 g, 5.65 mmol) and 3-butyryl-4-chloro-8-methoxyquinoline (1.23 g, 8.48 mmol) in dioxan (50 ml) were refluxed under nitrogen for 2.5 hours. The solvent was evaporated and the product was converted to the free base, purified by flash chromatography (silica, methanol-ammonia/chloroform), triturated with methanol, filtered, washed and dried to give the title compound (0.58 g), m.p. 274°–5° (dec).

$C_{20}H_{28}F_2N_2O_3 \cdot 0.15 CHCl_3$ 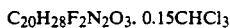

Found; C 61.87, H 4.67, N 7.18.
Requires; C 62.01 H 4.69, N 7.18.

EXAMPLE 15

Preparation of
3-butyryl-4-(3,4-dihydroxy-2,6-dimethylphenylamino)-8-methoxyquinoline

A. Preparation of cyclohexanone 4-amino-3,5-dimethyl-1,2-phenylene ketal

Cyclohexanone 4-nitro-3,5-dimethyl-1,2-phenylene ketal (10.0 g) and 10% palladium on charcoal (1.0 g) in ethanol (200 ml) was shaken in a hydrogen atmosphere (50 p.s.i.) at 45° C. for 3 hours. The mixture was filtered through celite and evaporated to leave cyclohexanone 4-amino-3,5-dimethyl-1,2-phenylene ketal (8.0 g, 90%) as a brown oil.

B. Preparation of the cyclohexanone ketal of 3-butyryl-4-(3,4-dihydroxy-2,6-dimethylphenylamino)-8-methoxyquinoline.

Cyclohexanone 4-amino-3,5-dimethyl-1,2-phenylene acetal (3.1 g, 13 mmol) and 3-butyryl-4-chloro-8-methoxyquinoline (2.75 g, 12 mmol) were heated together under reflux in 1,4-dioxan (50 ml) for 1.5 hours. The solvent was evaporated and the residue was dissolved in chloroform, washed with 2M HCl, sodium hydrogen carbonate solution and brine. Evaporation and crystallisation from ether gave 3-butyryl-4-(cyclohexanone-1-amino-2,6-dimethyl-3,4-phenylene acetal)-8-methoxyquinoline (2.2 g) as light brown crystals. Chromatography of the mother liquors gave an additional 1.0 g of the title compound (total 3.2 g, 57%), m.p. 151°–3°.

C. Preparation of
3-butyryl-4-(3,4-dihydroxy-2,6-dimethylphenylamino)-8-methoxyquinoline The product from B (1.0 g) in 5M hydrochloric acid (50 ml) was heated under reflux for 10 minutes, ensuring all the solid had dissolved. The mixture was cooled and carefully taken to pH7 by the addition of sodium hydrogen carbonate solution. The yellow solid which appeared was filtered off, washed with water, dichloromethane and ether and dried in vacuo to give 3-butyryl-4-(3,4-dihydroxy-2,6-dimethylphenylamino)-8-methoxyquinoline (0.75 g, 90%), m.p. 288°–90° C.

$C_{22}H_{24}N_2O_4$ 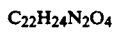

Found; C 69.32, H 6.40, N 7.21.
Requires; C 69.46, H 6.36, N 7.36.

EXAMPLE 16

Preparation of
3-butyryl-4-(4-hydroxy-2-methylphenylamino)-6-hydroxyquinoline

A. Preparation of ethyl 2-butyryl-3-(4-methoxyphenylamino)acrylate

4-Methoxyaniline (25 g) and ethyl 2-butyryl-3-ethoxyacrylate (57 g) were heated together on a rotary evaporator (bath temp 100°) for 1 hour to give ethyl 2-butyryl-3-(4-methoxyphenylamino)acrylate (78 g) as an orange oil.

B. Preparation of 3-butyryl-6-methoxy-4(1H)-quinolone

Ethyl 2-butyryl-3-(4-methoxyphenylamino)acrylate (78 g) was added dropwise to boiling diphenyl ether (600 ml) and heating continued under reflux for 45 minutes. When cool, the mixture was diluted with petrol and the precipitate was filtered off, washed with petrol and dried to give 3-butyryl-6-methoxy-4(1H)-quinolone (24 g, 49%) as a light tan solid, m.p. 252°–254°.

C. Preparation of 3-butyryl-4-chloro-6-methoxyquinoline

3-Butyryl-6-methoxy-4(1H)-quinolone (20 g) was heated under reflux in phosphorus oxychloride for 1 hour. The mixture was cooled, poured onto ice and carefully neutralized with ammonia solution. The mixture was extracted with dichloromethane and the combined extracts washed with sodium hydrogen carbonate solution (×2) and brine. The organic solution was dried, filtered and evaporated to give 3-butyryl-4-chloro-6-methoxy-quinoline (13.3 g, 62%) as an oil which crystallized from ether/petrol; m.p. 73°–75°.

D. Preparation of 3-butyryl-4-chloro-6-hydroxyquinoline

3-Butyryl-4-chloro-6-methoxyquinoline (7.9 g) was stirred in dry dichloromethane (150 ml) under nitrogen and boron tribromide (8.5 ml) was added via a syringe. The mixture was stirred overnight then cautiously added to a large volume of ice. The mixture was taken to pH 14 with sodium hydroxide solution, washed with dichloromethane, neutralized with hydrochloric acid and extracted several times with dichloromethane. The combined extracts were washed with brine, dried, filtered and evaporated to give 3-butyryl-4-chloro-6-hydroxyquinoline as a yellow powder (1.5 g, 20%) m.p. 157°–160°.

E. Preparation of 3-butyryl-4-(4-hydroxy-2-methylphenylamino)-6-hydroxyquinoline 3-Butyryl-4-chloro-6-hydroxyquinoline (4.0 g) and 4-amino-m-cresol (2.0 g) were heated together under reflux in 1,4-dioxan (60 ml) for 2 hours. The solvent was evaporated and the residue was dissolved in chloroform and washed successively with 2M HCl, sodium hydrogen carbonate solution (×2) and brine. The organic solution was dried, filtered and evaporated to a brown oil. A quantity of solid material that appeared insoluble in chloroform was combined with the oil and the mixture was chromatographed (silica gel, 2–4% methanol in chloroform) to give 3-butyryl-4-(4-hydroxy-2-methylphenylamino)-6-hydroxyquinoline (1.3 g, 24%) as orange crystals, m.p. 242°–244°.

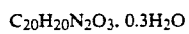

Found; C 70.26, H 5.89, N 8.21.
Requires; C 70.28, H 6.07, N 8.24.

EXAMPLE 17

Preparation of 3-butyryl-4-(4-hydroxy-2-methylphenylamino)-6-hydroxy-8-methoxyquinoline A. Preparation of 4-amino-3-methoxyphenol Sulphanilic acid (43.3 g) and anhydrous sodium carbonate (13.25 g) were dissolved in water (250 ml) and cooled to 15 C. Sodium nitrite (18.5 g) in water (100 ml) was added and the mixture was immediately poured onto a mixture of ice (300 ml) and hydrochloric acid (54 ml), and stirred at 0° for 20 minutes. The suspension was then added to a cooled solution of 3-methoxyphenol (31 g) and sodium hydroxide (55 g) in water (300 ml). The resulting deep red solution was stirred for 1 hour then heated to 70°. Sodium dithionite was added portionwise until the colour discharged on cooling, crystals of 4-amino-3-methoxyphenol (23 g, 66%) formed which were filtered, washed with water and dried, m.p. 168°–170°.

B. Preparation of ethyl 2-butyryl-3-(4-hydroxy-2-methoxyphenylamino)acrylate

4-Amino-3-methoxyphenol (21 g) and ethyl 2-butyryl-3-ethoxyacrylate (36 g) were heated together at 90°–110° for 30 minutes to afford ethyl 2-butyryl-3-(4-hydroxy-2-methoxyphenylamino)acrylate (46.1 g, 77%) as a brown solid, m.p. 140°–142°.

C. Preparation of ethyl 2-butyryl-3-(4-benzoyloxy-2-methoxyphenylamino)acrylate

Ethyl 2-butyryl-3-(4-hydroxy-2-methoxyphenylamino)acrylate (34.5 g) and pyridine (100 ml) were stirred in dichloromethane (500 ml) at 0°–5°. Benzoyl chloride (20 ml) in dichloromethane (100 ml) was added dropwise (below 10°) and the mixture was stirred overnight at room temperature. The reaction mixture was washed successively with water, 2M HCl (×2) and sodium hydrogen carbonate solution (×2). The organic layer was dried, filtered and evaporated to an oil which crystallized on standing to give ethyl 2-butyryl-3-(4-benzoyloxy-2-methoxyphenyl-amino)acrylate (24 g, 52%) m.p. 85°–87°.

D. Preparation of 3-butyryl-6-benzoyloxy-8-methoxy-4(1H)-quinolone

Ethyl 2-butyryl-3-(4-benzoyloxy-2-methoxyphenylamino)acrylate (22 g) was added portionwise to boiling diphenyl ether and heated under reflux for 45 minutes. When cool, the mixture was chromatographed (silica gel, 2% methanol in dichloromethane) to give 3-butyryl-6-benzoyloxy-8-methoxy-4(1H)-quinolone as a light brown solid (18.1 g, 92%), m.p. 102°–4°.

E. Preparation of 3-butyryl-6-benzoyloxy-4-chloro-8-methoxyquinoline

3-Butyryl-6-benzoyloxy-8-methoxy-4(1H)-quinolone (18.0 g) was heated under reflux in phosphorus oxychloride (100 ml) for 40 minutes. The solvent was evaporated and the residue dissolved in dichloromethane and poured into a vigorously stirred mixture of ice and sodium hydrogen carbonate solution. The organic phase was washed with sodium hydrogen carbonate solution, dried, filtered and evaporated to give 3-butyryl-6-benzyloxy-4-chloro-8-methoxy quinoline as a brown oil (25 g).

F. Preparation of 3-butyryl-4-(4-hydroxy-2-methylphenylamino-6-hydroxy-8-methoxyquinoline 3-Butyryl-4-chloro-6-benzoyloxy-8-methoxyquinoline (6.0 g) and 4-amino-m-cresol (2.0 g) were heated together under reflux in 1,4-dioxan (100 ml) for 2 hours. The solvent was evaporated and the residue heated on a steam bath in 10% methanolic potassium hydroxide for ten minutes. The solution was neutralized with 5M HCl and extracted several times with dichloromethane. The combined extracts were dried and evaporated to give 3-butyryl-4-(4-hydroxy-2-methylphenylamino)-6-hydroxy-8-methoxyquinoline (4.0 g, 70%) m.p. 251°–253°.

EXAMPLE A

A tablet for oral administration is prepared by combining

|  | Mg/Tablet |
|---|---|
| Compound of structure (I) | 100 |
| lactose | 153 |
| Starch | 33 |
| crospovidone | 12 |
| microcrystalline cellulose | 30 |
| magnesium stearate | 2 |
|  | 330 mg | into a 9 mm tablet.

EXAMPLE B

An injection for parenteral administration is prepared from the following

|  | % w:w |
|---|---|
| Compound of structure (I) | 0,50% (w:v) |
| IM citric acid | 30% (v:v) |
| sodium hydroxide (qs) | to pH 3.2 |
| water for injection EP | to 100 ml |

The compound of structure (I) is dissolved in the citric acid and the pH slowly adjusted to pH 3.2 with the sodium hydroxide solution. The solution is then made up to 100 ml with water, sterilised by filtration and sealed into appropriately sized ampoules and vials.

Biological Data

H+K+ATPase Activity

The effects of a single high concentration (100M) of a compound of structure (I) on K+-stimulated ATPase activity in lyophilised gastric vesicles was determined. Preferred compounds of structure (I) were also tested over a range of concentrations to determine IC$_{50}$ values.

(i) Preparation of lyophilised gastric vesicles (H/K-ATPase)

Lyophilised gastric vesicles were prepared from pig fundic mucosa after the method of Keeling et. al. (Biochem. Pharmacol, 34, 2967, 1985).

(ii) K+-stimulated ATPase activity

K+-stimulated ATPAse activity was determined at 37° C. in the presence of the following: 10 mM Pipes/Tris buffer pH 7.0, 2 mM MgSO$_4$, 1 mM KCl, 2 mM Na$_2$ATP and 3–6 g protein/ml lyophilised gastric vesicles. After incubation for 30 minutes, the inorganic phosphate hydrolysed from ATP was determined by the method of Yoda and Hokin (Biochem. Biophys, Res. Commun. 40, 880, 1970).

Compounds of structure (I) were dissolved in dimethylsulphoxide which up to the highest concentration used had no effect on K+-stimulated ATPase activity.

The effect of the highest concentration of each compound of structure (I) on the recovery of a standard amount of inorganic phosphate was also determined.

The results obtained were as follows:

| Compound | IC$_{50}$(M) |
|---|---|
| 1 | 0.67 |
| 2 | 0.21 |
| 3 | 0.50 |
| 6 | 0.71 |
| 7 | 0.55 |
| 9 | 0.08 |
| 12 | 0.16 |
| 15 | 2.80 |
| 16 | 0.07 |
| 17 | 1.30 |

What is claimed is:

1. A compound of structure (I):

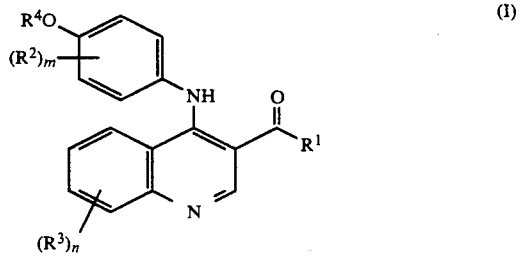

wherein
R$^1$ is hydrogen, C$_{1-6}$alkyl, -C$_{1-6}$alkoxy;
R$^2$ is hydrogen, C$_{1-6}$alkyl or halogen;
m is 1 or 2;
R$^3$ is hydrogen, halogen, C$_{1-6}$alkoxy or C$_{1-6}$alkanoyl;
n is 1; and
R$^4$ is hydrogen;
or a salt thereof.

2. The compound according to claim 1 wherein the halogen is fluorine.

3. The compound according to claim 1 wherein the halogen is chlorine.

4. The compound according to claim 1 wherein m is 1.

5. The compound according to claim 1 which is 3-butyryl-4-(4-hydroxyphenylamino)-8-methoxyquinoline.

6. The compound according to claim 1 which is 3-butyryl-4-(4-hydroxy-2-methylphenylamino)-8-methoxyquinoline.

7. The compound according to claim 1 which is 3-butyryl-4-(4-hydroxy-2,6-dimethylphenylamino)-8-methoxyquinoline.

8. The compound according to claim 1 which is 3-butyryl-4-(4-hydroxy-3-fluorophenylamino)-8-methoxyquinoline.

9. The compound according to claim 1 which is 3-butyryl-4-(3-chloro-4-hydroxyphenylamino)-8-methoxyquinoline hydrochloride.

10. The compound according to claim 1 which is 3-butyryl-4-(4-hydroxy-2-methylphenylamino)-8-fluoroquinoline.

11. The compound according to claim 1 which is 3-butyryl-4-(4-hydroxy2-methylphenylamino)-8-acetylquinoline.

12. A compound which is 3-butyryl-4-(4-acetoxy-2-methylphenylamino)-8-methoxyquinoline.

13. A pharmaceutical composition comprising a compound according to claim 7 or a pharmaceutically acceptable salt thereof and a pharmaceutically acceptable carrier.

14. A method of inhibiting gastric acid secretion which comprises administering to a mammal in need thereof an effective amount of a compound according to claim 1.

15. A method of treatment of gastrointestinal diseases and other conditions caused or exacerbated by gastric acidity which comprises administering to a mammal in need thereof an effective amount of a compound according to claim 1.

16. The compound according to claim 1 wherein $R^1$ is $C_{1-6}$alkyl, or $C_{1-6}$alkoxy.

17. The compound according to claim 1 wherein $R^2$ is selected from hydrogen, or $C_{1-6}$alkyl and is in the 2-position of the quinoline ring.

18. The compound according to claim 1 wherein $R^3$ is $C_{1-6}$alkoxy and is in the 8-position of the quinoline ring.

* * * * *